US006955914B2

(12) United States Patent
Yang

(10) Patent No.: US 6,955,914 B2
(45) Date of Patent: Oct. 18, 2005

(54) METHOD FOR MAKING A MOLECULARLY SMOOTH SURFACE

(75) Inventor: Xing Yang, San Diego, CA (US)

(73) Assignee: GeneOhm Sciences, Inc., San Diego, CA (US)

( * ) Notice: Subject to any disclaimer, the term of this patent is extended or adjusted under 35 U.S.C. 154(b) by 152 days.

(21) Appl. No.: 10/121,240

(22) Filed: Apr. 10, 2002

(65) Prior Publication Data

US 2003/0194710 A1 Oct. 16, 2003

(51) Int. Cl.⁷ ............................................. C12M 1/34
(52) U.S. Cl. ........................ 435/287.2; 435/6; 451/41; 438/758; 536/23.1; 422/68.1; 422/82.01; 422/82.02; 422/99
(58) Field of Search ..................... 435/6, 91.1, 287.2; 536/23.1; 216/23; 205/118; 438/106, 609, 758; 252/62; 451/41; 422/68.1, 82.01, 82.02, 99

(56) References Cited

U.S. PATENT DOCUMENTS

| | | | |
|---|---|---|---|
| 4,942,127 A | | 7/1990 | Wada et al. |
| 4,963,815 A | | 10/1990 | Hafeman |
| 5,312,527 A | * | 5/1994 | Mikkelsen et al. ...... 205/777.5 |
| 5,776,672 A | * | 7/1998 | Hashimoto et al. ............ 435/6 |
| 5,972,692 A | * | 10/1999 | Hashimoto et al. ...... 435/285.2 |
| 5,993,634 A | | 11/1999 | Simpson et al. |
| 6,087,102 A | | 7/2000 | Chenchik et al. |
| 6,169,394 B1 | | 1/2001 | Frazier et al. |
| 6,200,761 B1 | * | 3/2001 | Meade et al. ................... 435/6 |
| 6,203,758 B1 | | 3/2001 | Marks et al. |
| 6,221,586 B1 | * | 4/2001 | Barton et al. .................... 435/6 |
| 6,336,845 B1 | * | 1/2002 | Engdahl et al. ............... 451/41 |
| 6,340,374 B1 | * | 1/2002 | Kato et al. ..................... 51/308 |
| 6,343,976 B1 | * | 2/2002 | Yoshida et al. ............... 451/41 |
| 6,347,997 B1 | * | 2/2002 | Armstrong .................... 463/37 |
| 6,354,912 B1 | * | 3/2002 | Osada et al. .................. 451/41 |
| 6,354,913 B1 | * | 3/2002 | Miyashita et al. ............ 451/41 |
| 6,610,230 B2 | * | 8/2003 | Jiang et al. ................. 264/161 |
| 6,780,786 B2 | * | 8/2004 | Dougherty .................. 438/758 |
| 2002/0185466 A1 | * | 12/2002 | Furuta et al. .................. 216/23 |
| 2003/0070931 A1 | * | 4/2003 | Kitchens ..................... 205/118 |
| 2003/0082847 A1 | * | 5/2003 | Turner et al. ............... 438/106 |
| 2003/0089880 A1 | * | 5/2003 | Ishida et al. .................. 252/62 |
| 2003/0124853 A1 | * | 7/2003 | Oi ............................. 438/690 |
| 2003/0127422 A1 | * | 7/2003 | Tsuchiya ....................... 216/2 |

OTHER PUBLICATIONS

International Preliminary Examination Report mailed Apr. 15, 2005.
Goss, et al. "Application of (3–Mercaptopropyl) trimethoxysilane as a Molecular Adhesive in the Fabrication of Vapor–Deposited Gold Electrodes on Glass Substrates", Analytical Chemistry, 63, pp. 85–88, (1991).
International Search Report for International Application No. PCT/US03/11227, dated Aug. 6, 2004.

* cited by examiner

Primary Examiner—Bradley L. Sisson
(74) Attorney, Agent, or Firm—Knobbe, Martens, Olson, & Bear LLP

(57) ABSTRACT

A method is provided for making a molecularly smooth surface, preferably on an electrode of an assay chip. This is desirable because it allows molecules, preferably oligonucloetides, to attach to the electrode surface with greater reliability and packing density than was previously available. Such attachment of molecules to an electrode surface is of particular interest in the field of electrochemical genetic analysis.

11 Claims, 2 Drawing Sheets

METHOD FOR MAKING A MOLECULARLY SMOOTH SURFACE

BACKGROUND OF THE INVENTION

1. Field of the Invention

This invention relates to methods for making smooth surfaces for microelectronic and chemical/biological assay applications. In a preferred embodiment, a gold electrode is created having a substantially molecularly smooth surface; the electrode is part of a genetic analysis chip and an oligonucleotide can be attached to the smooth surface.

2. Description of the Related Art

Many technologies use electrical circuit contacts embedded or otherwise attached to a substrate. Many of these further provide for attaching molecules, particularly complex biological molecules, to an electrical contact surface. For example, in the field of genetic analysis, strands of oligonucleotides such as DNA are commonly attached to the surface of an electrode (e.g., U.S. Pat. Nos. 5,312,527; 5,776,672; 5,972,692; 6,200,761; 6,221,586.) Other biological and nonbiological sensors and assay devices similarly utilize sensor molecules (such as enzymes or receptors) attached to an electrode.

For molecules such as DNA to attach uniformly and reliably to the surface of an electrode, it is desirable that the electrode surface be as smooth as possible, ideally, the surface would be atomically smooth.

Presently, there are several methods for making electrode surfaces by depositing a conductive layer on a substrate. For example, gold and other metals have been deposited on semiconductor substrates using methods such as evaporation, sputtering, and electroplating. Unfortunately, these methods typically create a metal layer with a top surface that is too rough for some applications. For example, an evaporated gold surface can have a roughness as high as 200 Å. This roughness on the surface can change the packing density of of DNA molecules deposited on the gold surface and significantly affect the structural integrity of DNA monolayers formed on the gold surface.

Hence, there exists a need for a method of creating very smooth surfaces on materials capable of conducting electrical current. In particular, there exists a need in the genetic analysis field and in other assay devices for a method of creating an electrode surface on a substrate where that surface is substantially molecularly smooth.

SUMMARY OF THE INVENTION

One aspect of the invention is a method for making a substantially molecularly smooth surface on a layer by depositing that layer against a substrate having a substantially molecularly smooth surface.

Another aspect is method for making a substantially molecularly smooth attachment surface, including the steps of: providing a substrate that is smooth to within about 10 atomic diameters of the substrate material; applying an attachment material to the smooth substrate; and etching away at least a portion of the substrate to reveal a smooth matching surface of the attachment material. Preferably, the attachment material can act as an electrode and may contain gold, carbon, or another appropriate material. Further, an assay reagent or a binding moiety can be attached to the smooth surface. This assay reagent can contain DNA, RNA, an enzyme, an antigen, a peptide, a peptidomimetic, an antibody, other types of specific binding molecules, a substrate, a native, recombinant, or chimeric receptor, a chemical reagent, a redox moiety, a chemical or biological sensor or sensor molecule, an organic chemical compound, and the like. In a preferred embodiment, the assay reagent contains DNA.

Another aspect of the invention includes attaching a supporting layer to the attachment material on a surface opposite the smooth matching surface. Another aspect of the invention includes etching away the substrate to reveal a molecularly smooth attachment surface in a plurality of locations.

Another aspect of the invention is an assay chip having a first surface and a second surface, featuring: a substrate layer having a first surface and a second surface corresponding respectively in location to the first surface and second surface of the assay chip, wherein the second surface of the substrate is smooth to within 10 atomic diameters of the substrate; at least one conductor deposited on the second surface of the substrate; an assay region accessible from the first surface of the substrate, in which the substrate has been etched away to expose a portion of conductor; and one or more assay reagents attached to the conductor in the assay region. The conductor on the assay chip may contain gold, carbon or another appropriate material. Preferably, the assay chip features a plurality of conductors and assay regions. The assay chip can also contain an array of electrodes. In a preferred embodiment, the assay reagent contains a nucleotide, such as DNA or RNA.

Another aspect of the invention is a method for conducting an assay, including: providing an assay chip having a plurality of assay reagents attached to one or more conductors in different assay regions; flooding the first surface of the assay chip with an aqueous sample, such that the sample contacts a plurality of said assay regions; and measuring an electrical signal resulting from the interaction of analyte, if present in the sample, with at least one reagent. The assay chip used for this method can contain a plurality of conductors and an electrical signal may be measured through a circuit utilizing one or more of those conductors.

DETAILED DESCRIPTION OF THE PREFERRED EMBODIMENTS

Figure 1A:
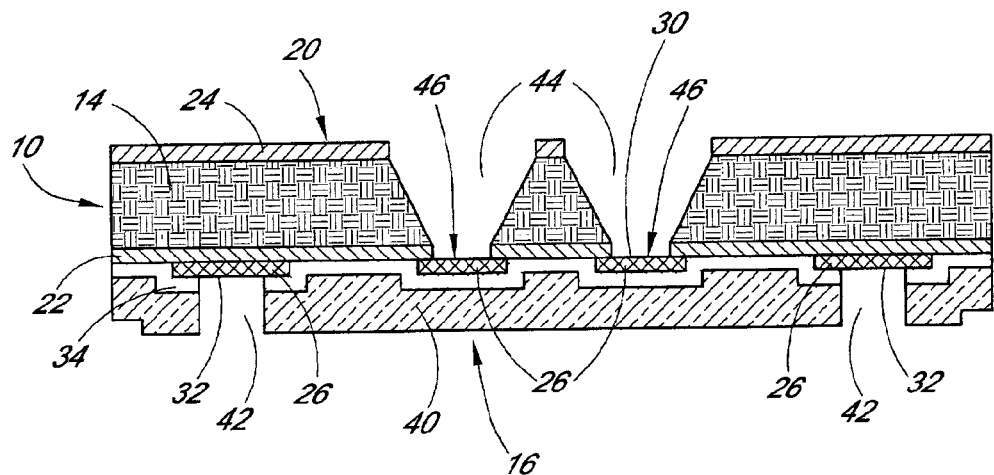
FIGS. 1a–1b are cross-sectional views of two DNA chips of the present invention. Both show the reagent reservoirs accessible from the top while the electrical contact electrodes are accessible from the underside of the chip.

In the present disclosure, various methods and apparatus are provided for preparing electrodes having a substantially molecularly smooth electrode surface. Although the present disclosure describes the inventions primarily in the context of DNA chips, it will be understood and appreciated that many aspects of the disclosure are applicable to other technologies (including most chemical and biological assay devices having molecules attached to an electrode) in which a substantially molecularly smooth electrode surface is desirable. Thus, in addition to DNA, the bound assay reagent can include, without limitation, an enzyme, RNA, an antigen, a peptide, a peptidomimetic, an antibody, other types of specific binding molecules, a substrate, a native, recombinant, or chimeric receptor, a chemical reagent, a redox moiety, a chemical or biological sensor or sensor molecule, an organic chemical compound, and the like. Thus, except as specifically required in the claims, the references to DNA and DNA chips are to be considered exemplary, not limiting.

In one aspect of the present invention, the assay chip is particularly suited for use in electrochemical analysis. In these embodiments, the invention includes an assay device having a substrate and one or more electrodes, at least one of which has a substantially molecularly smooth surface, with a reagent attached to said surface.

A. Chip Design and Fabrication

In the chip fabrication industry generally, when a layer is deposited on a substrate, the new outer surface of that layer has a roughness that depends on the method of the deposition. However, the interior surface of the deposited layer (the side adjacent to the substrate) generally has a roughness that mirrors that of the substrate. Hence, a substrate with a smooth surface can serve as a template to create a correspondingly smooth surface on a layer deposited against it.

One aspect of the invention is to use this interior surface principle to create an electrode having a smooth surface. In one embodiment, a conductive metal such as gold is deposited on a substantially molecularly smooth substrate. A supporting layer is attached so as to sandwich the metal between the substrate and the supporting layer. A portion of the substrate is then etched away to expose a region of metal. This newly exposed metal region has a surface that is substantially molecularly smooth.

The term "molecularly smooth" means that surface irregularities are primarily less than about 20 atomic diameters in height from the average height of the surface, and more preferably less than about 15, 10, 8, 7, 5, 3, or 2 atomic diameters in height. For gold, which has a covalent radius of 1.5 angstroms, a molecularly smooth surface would preferably have surface irregularities of less than about 45, 30, 25, 20, 15, 10, 8, 7, 5, or 3 angstroms in height from the average height of the surface.

A preferred embodiment of this invention is a DNA chip featuring a silicon substrate. An array of gold electrodes sandwiched between two layers of silicon dioxide insulator is attached to the silicon substrate. Opposite the silicon substrate is a supporting layer. The chip is oriented such that the silicon substrate is on the top and the supporting layer is on the bottom. Windows on the top (through the silicon substrate and top layer of insulator) allow access to the molecularly smooth surfaces of the reagent electrodes. These windows on the top can be referred to as "reagent reservoirs" which will receive liquid reagents during an assay. Windows on the underside (etched through the supporting layer and the bottom layer of insulator) allow access to the electrical contact electrodes. The two types of electrodes in the chip are selectively interconnected by deposited gold wiring within the insulating layer or by other methods known in the art. Access to a reagent electrode and an electrical contact electrode allows a complete circuit to be formed which will enable standard techniques in the art (such as resistance measurements) to be performed using the chip.

Techniques for polishing silicon to a molecularly smooth surface are well known in the art. For example, one appropriate technique involves polishing a single crystal silicon wafer progressively with a polishing slurry containing progressively smaller abrasive particles. Suitable methods for preparing silicon and other smooth substrates are disclosed, for example, in U.S. Pat. Nos. 6,354,913, 6,347,977, 6,343,976, 6,340,374, and 6,336,845.

FIG. 1A shows one embodiment of the chip 10 of the present invention. This Figure is a cross-section of a chip 10 having two reagent reservoirs 44, each of which contains a reagent electrode 30 having a substantially molecularly smooth surface 46. In this figure, the chip is oriented so that the reservoirs could receive reagents in a liquid deposited from above. Gravity would then hold the reagents in the reservoir to contact the smooth surface 46 of the reagent electrode 30. Chemical and/or biological reagents can thereby be attached to the smooth surface 46 as part of performing an assay involving said reagents. The illustrated embodiment shows only two reservoirs for ease of illustration, not by way of limitation. It will be understood that in many embodiments of the invention, the chip 10 will have many more assay reservoirs, e.g., 5, 10, 20, 30, 50, 100, 200, 1000 or more regions. These assay reservoirs are preferably arranged into a regular two-dimensional array.

The chip 10 includes a substrate 14 serving as the body of the chip. The substrate can be made of silicon, including monocrystalline and polycrystalline silicon, preferably of semiconductor grade. Alternatively, it can constitute plastic or other polymer material, glass, or composite material, including any of the common printed circuit board materials. In the illustrated embodiment, the substrate 14 preferably includes one or more insulating layers 22 and 24 of silicon dioxide or other suitable dielectric material. This is particularly useful when the substrate 14 is silicon, and is not necessarily required when the substrate 14 is itself a dielectric material. In FIG. 1A, a substrate 14 is shown, having a top 20 and a bottom 16. Two insulating layers 24 and 22 are respectively shown on the top 20 and a bottom 16 of the substrate. It is important to note that during the fabrication process illustrated infra that the top is initially 16 and the bottom is initially 20. During the fabrication process, the chip is turned over to complete the manufacturing process ultimately making 20 the top and 16 the bottom when the chip is in use.

One or more electrodes 26 are formed on an insulating layer 22. Some of these electrodes are reagent electrodes 30 and some are electrical contact electrodes 32. The reagent electrodes have an exposed substantially molecularly smooth surface 46 to which reagents can be attached as part of performing an assay. Typically, at least one, and sometimes two or more reagent electrodes 30 are formed in each reagent reservoir 44.

The first insulating layer 22 insulates the electrodes from the silicon substrate. The electrodes are advantageously formed of gold or other noble metal, but may be any conductive material onto which reagent may be affixed, including without limitation, platinum, palladium, rhodium, carbon electrodes such as glassy carbon, oxide electrodes, or semiconductor electrodes. The electrodes may also contain conductive polymers on the surface. Gold electrodes are particularly preferred. The reagent electrodes 30 are joined to electrical conductors (not shown in this cross section) that form a conductive path to a desired connection point or electrical contact electrode 32. The connection could also be made by any other method of electrical interface known in the art. As different reservoirs can contain different reagents, it is desirable that each reagent electrode correspond to a single electrical contact electrode for independent measurements. Note that the connection points or contact electrodes 32 can be located on the back side of the device, on an edge of the device, or on the face of the device, or (when the conductor is a wire) at a point remote from the device.

Preferably, a second insulating layer 34 is formed over the first insulating layer 22 and the gold layer 26, further isolating the gold layer 26 from exposure. The second insulating layer 34 may advantageously be formed of silicon dioxide, but other insulating materials, including polymers, may be used in various embodiments of the chip 10. For example, if the substrate 14 is a printed circuit board substrate, a conformal insulating coating may be used.

A supporting layer 40 is also advantageously attached to the underside of the chip. This layer further protects the gold layer and provides structural support to the chip where the substrate layer 14 is etched away (as in the locations of the reagent reservoirs 44.) The supporting layer can be photoresist, polyimide, Parylene, or other suitable material. Electrical contact windows 42 are preferably patterned through the supporting layer 40 and the second insulating layer 34 to provide electrical connections to the electrical contact electrodes 32.

Figure 1B:
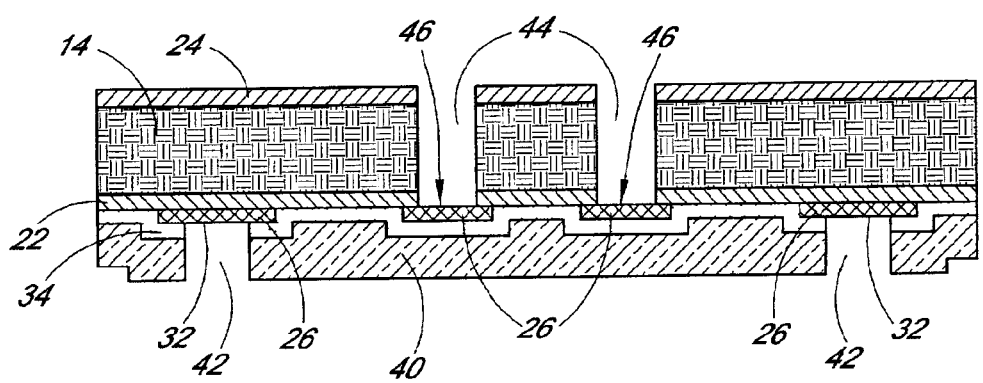

FIG. 1B similarly shows a cross section of one embodiment of the assay chip. The difference between FIGS. 1A and 1B is in the shape of the reagent reservoirs 44. In FIG. 1A the reservoirs were etched using a silicon anisotropic etching agent such as potassium hydroxide solution (a bulk micromachining process); in FIG. 1B, the reservoirs were etched using a deep reactive ion etching technology (DRIE, U.S. Pat. No. 5,501,893). The differences in these techniques are discussed in greater detail infra.

During fabrication of the chip, a plurality of different reagents may advantageously be deposited into the different reservoirs 44 and on the reagent electrode surfaces 46 of the chip 10. These reagents are typically contained in microdroplets of a liquid, preferably an aqueous liquid, and thus dry very quickly to deposit the reagent onto the surfaces 46 of the reagent electrodes 30. For attaching DNA, for example, a thiol-derivatized polynucleotide strand will covalently bond to the gold electrode under well-known incubation conditions. Any of the other well known or otherwise suitable techniques for bonding an assay molecule to an electrode can also be used. The reagent or assay molecule can be connected directly to the electrode, or can be connected to the electrode through a linking molecule or layer of molecules.

The assay chips of the present invention are useful for a variety of procedures. By using a precisely controlled robotic system, drops of solution with DNA molecules in precise volume can be deposited onto some or all of the reagent reservoirs. Robotic or computer-controlled spotting devices can be used for this process. Because the reservoirs are isolated from each other, DNA molecules with different sequences (or other different reagents) can be deposited onto adjacent reservoirs without mixing.

Figure 2A:
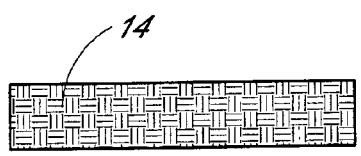
FIGS. 2a–2h are cross-sections of silicon wafers being manufactured into DNA chips according to the present invention, illustrating the progressive etching and deposition steps in the manufacturing process.
Figure 2E:
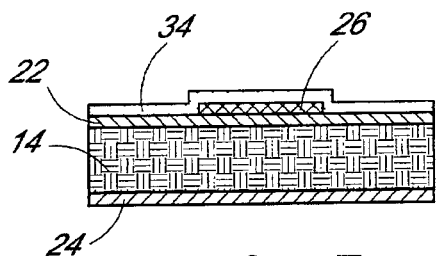
Figure 2B:
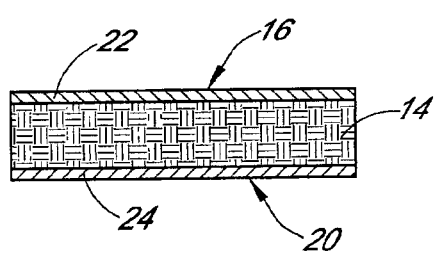

FIGS. 2A through 2H illustrate the progressive stages of one exemplary fabrication process using silicon wafers. The process starts in FIG. 2A with a 4 inch single crystalline silicon wafer substrate 14 with <100> orientation. With reference to FIG. 2B, top and bottom layers 22 and 24 of silicon dioxide are grown on the top 16 and bottom 20 of the wafers. Note that the top 16 and bottom 20 during fabrication will respectively become the bottom and top when the chip is in use. The bottom layer 24 is preferably 1.5 μm thick which can be achieved by silicon dioxide growth at 1050 C. for 6 hours.

The top face 16 of top layer 22 should be substantially molecularly smooth as it will define the smoothness of the electrodes deposited thereon. This smoothness can be achieved using any of several methods. One method is to make the silicon dioxide layer 22 very thin so that it will approximate the smoothness of the underlying substrate 14. For this method, the surface of the substrate 14 should be made substantially molecularly smooth using techniques known in the art. The thickness of the silicon dioxide layer 22 is preferably in the range of 50 to 100 Å.

An alternative method for making the top surface 16 of layer 22 substantially molecularly smooth is to use chemical mechanical polish (CMP). For this technique, layer 22 should be relatively thick; approximately 2 μm thick is preferred. Once this silicon dioxide layer is grown, it can be made smoother using standard CMP methods known in the art. Other standard techniques for making smooth surfaces on dielectric materials can also be used.

Figure 2F:
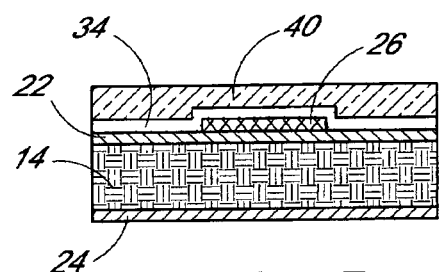
Figure 2C:
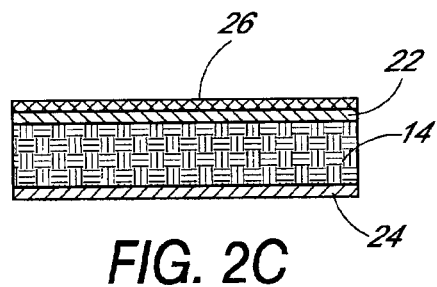

Next, with reference to FIG. 2C, a layer 26 of 50 Å chromium and 3000 Å gold is thermally evaporated onto the wafers 14. The chromium layer is not strictly necessary, but is preferred as it serves as an adhesion layer to improve the adhesion of gold to silicon dioxide. Titanium can also be used in place of chromium in the adhesion layer between the silicon dioxide and the gold. Alternatively, many insulating organic coupling agents such as organofunctional silanes can be used to improve adhesion of gold to silicon dioxide. See Charles A. Goss, Deborah H. Charych, and Marcin Majda, "Application of (3-Mercaptopropyl) trimethoxysilane as a Molecular Adhesive in the Fabrication of Vapor-Deposited Gold Electrodes on Glass Substrates," Analytical Chemistry, 63, pp. 85–88, 1991. Next, with reference to FIG. 2D, the chromium/gold layer 26 is patterned and etched with chromium and gold etchants to define the electrodes and conductors. The electrodes can ultimately serve either as reagent contacts 30 or electrical contacts 32. Those of skill in the art will recognize that the layout of the two types of contacts and the conductors which selectively interconnect them will depend on the size and intended use of the assay chip.

Next, as illustrated in FIG. 2E, a layer of 3000 Å thick silicon dioxide is deposited on the wafers in a low pressure chemical vapor deposition (LPCVD) reactor at 450 C. for 30 minutes, to form a second top insulating layer 34. This layer of silicon dioxide is often referred as low temperature oxide (LTO) in the semiconductor industry. The LTO procedure can be done at other temperatures and for different thicknesses. The time required to reach a desired thickness is typically a function of the chosen temperature.

Next, with reference to FIG. 2F, a supporting layer 40 is applied to the chip. This layer provides structural support for the chip 10 when the original silicon substrate 14 is etched from the opposite side. The supporting layer 40 can be made from any suitable material provided it can be attached to the chip and is rigid enough to maintain its shape against the stresses that will be experienced by the chip. The supporting layer can be photoresist, polyimide, Parylene, silicone rubber, Teflon, or other suitable polymer material. Other compounds which are common in the industry can also be used such as poly or amorphous silicon, silicon dioxide, and silicon nitride. The supporting layer should be thick enough to hold the electrodes in place and to resist the anticipated stresses (associated with normal use) that could bend or break the chip, but not so thick as to be unreasonably difficult to etch. Alternatively, when flexible substrates and other chip materials are used, the entire device can be made flexible to minimize the possibility of breakage.

The supporting layer can be attached to the chip using a variety of techniques which are known in the art. Polymer materials can be spin coated as liquids and then baked. Parylene can be vapor deposited. Silicon and silicon compound materials can be sputtered or chemical vapor deposited (CVD). Other standard techniques can also be used.

Figure 2G:
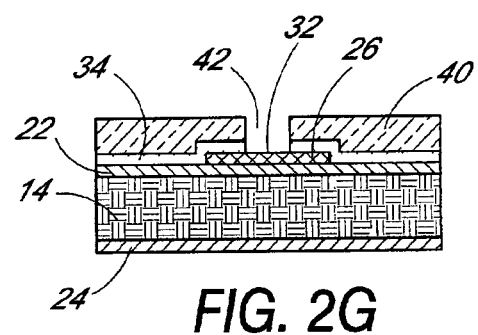
Figure 2D:
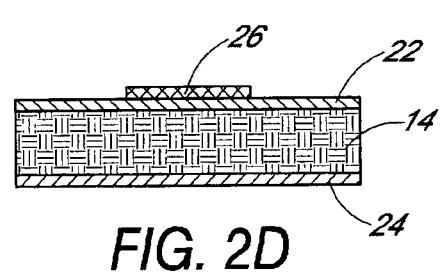

With reference to FIG. 2G, electrical contact windows 42 to selected electrical contact electrodes 32 are etched through the supporting layer 40 and the LTO layer 34. The supporting layer can be etched in several ways. Most polymer materials can be plasma etched. Silicon and silicon compound materials can be etched by common methods in the industry such as plasma based etching and wet chemical etching. After etching through the supporting layer 40, the LTO layer 34 can be etched to complete the window 44 and reach the electrical contacts 32. The LTO layer 34 can be patterned and etched with buffered hydrofluoride acid thereby exposing the electrical contact gold electrodes on what will ultimately be the underside of the chip.

Figure 2H:
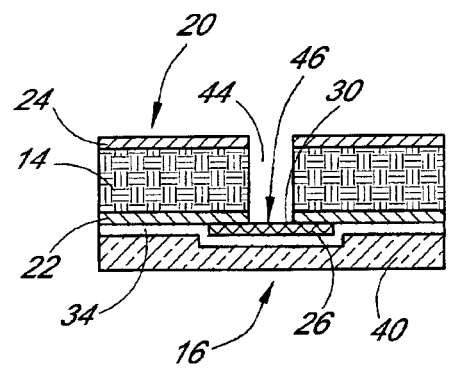

With reference to FIG. 2H, the chip is flipped over to the orientation in which it will ultimately be used. On the top side 20 of the chip (formerly the underside 20), the reagent windows 44 are etched through the first insulating layer 24, the silicon substrate 14, and the second insulating layer 22 to reach selected reagent electrodes 30. The insulating layers 24 and 22 can be etched with hydrofluoride acid. The silicon substrate 14 can be etched using a variety of techniques. The substrate 14 can be etched using a silicon anisotropic etching agent such as potassium hydroxide solution (this is commonly referred to as bulk micromachining). As shown in FIG. 1A, the anisotropic etching method produces a cavity that has an angle of 54.74 (defined by the <100> and <111> crystal planes of silicon.) This angle can limit the density of electrodes on the chip. For example, on 500 μm thick wafers, the cavities will be at least 700 μm by 700 μm. To make them smaller, thin wafers can be used. Alternatively, a deep reactive ion etching technology (DRIE, U.S. Pat. No. 5,501,893, can be used to etch the cavities 44. With DRIE, very high aspect ratio structures can be made through the silicon substrate. FIGS. 1B and 2H show reservoirs created using DRIE. The anisotropic etching technique is generally preferred as it is less expensive, but DRIE is preferred when making a high density array of electrodes on a chip.

After etching through these layers, the reagent electrode 30 is exposed at the bottom of the reagent reservoir 44. The surface of the exposed reagent electrode 30 mirrors the surface to which it was originally deposited, insulating layer 22. Hence, the reagent electrode 30 in the reagent reservoir 44 has the desirable, substantially molecularly smooth surface 46.

If a chromium layer was used as an adhesion layer, then the chromium layer will be exposed before reaching the gold layer. In technologies where an exposed gold surface is preferable to an exposed chromium surface (as is common when attaching oligonucleotides), it is desirable to etch away the chromium layer. This can be done using a wet chemical etchant, such as CR-14, available from Transene Co., 10 Electronics Ave., Danvers, Mass. 01923. Although some of the smoothness of the surface may be lost when the chromium layer is etched, the roughness of the gold layer will typically be no greater than the thickness of the chromium layer. Even where this roughness is at its maximum, the final product still has a smoothness that is a recognizable improvement over the prior art. Finally, the wafers are diced and ready for testing using standard techniques in the art.

In the fabrication process, many other alternative materials and processes can be used. First, the substrate can be glass or other ceramic material provided that it is flat and smooth. Second, the bottom thermally grown silicon dioxide can be replaced by silicon nitride, silicon dioxide deposited by other means, or other polymer materials provided that they are smooth and can stand the high temperature in the following evaporation step. Third, the conducting layer need not be gold, but can be any appropriate material such as platinum, palladium, rhodium, a carbon composition, an oxide, or a semiconductor. If gold is chosen, the layer can be evaporated, sputtered, or electroplated, provided that it is smooth. Fourth, the LTO layer can be replaced by spin-on dielectric materials (commonly used in semiconductor industry) or other polymer materials such as polyimide, Parylene, and etc. Fifth, the reagent and electrical connections can be on the same side of the chip or on adjacent sides, though the opposite side configuration (as described above) is preferred. Finally, the temperatures, times, and dimensions specifically recited herein can be altered to produce chips having substantially the same properties and functionality as will be appreciated by those of skill in the art.

Typically, in the performance of the assay, an interaction occurs between an analyte and a reagent in the reagent reservoir 44. In many suitable assays, this interaction creates or causes an electrical signal, such as an electrical current. See, e.g., U.S. Pat. Nos. 6,221,586 and 5,591,578. Moreover, in these and other assays, the reagent is attached through covalent or noncovalent means, preferably to the reagent electrode 30. While many techniques are known for effecting such attachment (e.g., antibody, avidin/biotin, or other specific interactions, hydrostatic interactions, hydrogen bonding, various covalent attachment schemes), one particularly preferred method for attachment when using a gold electrode is the gold/thiol interaction. As more specifically described in the above references, polynucleotide derivatized with a thiol group readily reacts with and attaches to gold surfaces. In one preferred embodiment, one strand each of a plurality of double-stranded DNAs are attached to a gold electrode using such thiol-mediated attachment. This results in a unique, tightly packed, ordered DNA monolayer. Then, as more fully set forth in U.S. Pat. No. 6,221,586, the non-thiol-derivatized strand of each duplex is removed, leaving an ordered array of single stranded DNA capture reagents on the gold electrode. This ordered molecular array is sufficiently cohesive and/or continuous as to substantially prevent contact between the gold electrode and moieties in solution having a charge opposite to that of DNA.

What is claimed is:

1. A method for making a substantially molecularly smooth attachment surface, comprising the steps of:

providing a substrate that is smooth to within about 10 atomic diameters of the substrate material;

applying an attachment material to the smooth substrate; and etching away at least a portion of the substrate to reveal a smooth matching surface of the attachment material.

2. The method of claim 1, further comprising attaching a third material to the smooth matching surface of the attachment material.

3. The method of claim 2, wherein the attachment material is a conductor.

4. The method of claim 3, wherein the third material is an assay reagent or a binding moiety for attaching an assay reagent to the conductor.

5. The method of claim 2 wherein the substrate comprises silicon.

6. The method of claim 2 further comprising attaching a supporting layer to the attachment material to a surface opposite the smooth matching surface.

7. The method of claim 2 wherein the attachment material comprises gold.

8. The method of claim 2 wherein the attachment material comprises carbon.

9. The method of claim 4 wherein the assay reagent comprises a polynucleotide.

10. The method of claim 4 wherein the assay reagent comprises DNA.

11. The method of claim 1 wherein the substrate is etched away to reveal a molecularly smooth attachment surface in a plurality of locations.

* * * * *